US008847002B2

(12) United States Patent
Goh et al.

(10) Patent No.: US 8,847,002 B2
(45) Date of Patent: Sep. 30, 2014

(54) ABSORBENT ARTICLE CONTAINING APERTURES ARRANGED IN REGISTRATION WITH AN EMBOSSED WAVE PATTERN

(75) Inventors: Priscilla Goh Eng Goh, Bukit Batok (SG); YeinSze Ong, Choa Chu Kang (SG); Meijia Ng, Ang Mo Kio (SG); SangWook Lee, Choa Chu Kang (SG); DooHong Kim, Woodlands (SG); Franz Aschenbrenner, Kastl (DE)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 532 days.

(21) Appl. No.: 13/111,167

(22) Filed: May 19, 2011

(65) Prior Publication Data

US 2012/0296304 A1    Nov. 22, 2012

(51) Int. Cl.
*A61F 13/512* (2006.01)
*A61F 13/511* (2006.01)

(52) U.S. Cl.
USPC ............ 604/378; 604/379; 604/380; 604/383

(58) Field of Classification Search
USPC .................................. 604/378, 379, 380, 383
See application file for complete search history.

(56) References Cited

U.S. PATENT DOCUMENTS

| | | | |
|---|---|---|---|
| 3,371,668 A | 3/1968 | Johnson | |
| 3,460,536 A | 8/1969 | Champaigne, Jr. | |
| 3,542,634 A | 11/1970 | Such et al. | |
| 3,560,601 A | 2/1971 | Johnson et al. | |
| 3,814,101 A | 6/1974 | Kozak | |

(Continued)

FOREIGN PATENT DOCUMENTS

| | | |
|---|---|---|
| EP | 1 022 007 B1 | 3/2006 |
| FR | 2915372 A1 | 10/2008 |

(Continued)

OTHER PUBLICATIONS

Abstract of Chinese Patent—CN1247733, Mar. 22, 2000, 1 page.

(Continued)

*Primary Examiner* — Jacqueline F. Stephens
(74) *Attorney, Agent, or Firm* — Dority & Manning, P.A.

(57) ABSTRACT

An absorbent article that contains a topsheet having embossed regions is provided. The embossed regions propagate in a longitudinal direction of the article in the form of a wave having one or more alternating crests (peaks) and troughs (valleys). Such a wave pattern helps slow down the flow of bodily fluid by directing it along a tortuous path defined by the densified edges rather than in a straight line. Among other things, this reduction in flow rate can help provide sufficient time for the absorbent core to absorb the fluid, which is particularly helpful when it is already partially filled with fluid. Nevertheless, bodily fluids can still sometimes pool near the crests and/or troughs and result in leakage. To help counteract this tendency, the present inventors have discovered that a plurality of apertures can be employed in the topsheet that are arranged in a column that generally extends in a longitudinal direction of the article. At least a portion of the apertures are located proximate to contiguous crests and/or contiguous troughs of the embossed region. Without intending to be limited by theory, it is believed that the registration of the apertures with contiguous crests and/or contiguous troughs of the embossed region puts them in a better position to receive bodily fluids that tend to pool around the embossed regions and thus reduce the likelihood of leakage.

16 Claims, 6 Drawing Sheets

(56) References Cited

U.S. PATENT DOCUMENTS

| | | |
|---|---|---|
| 3,881,490 A | 5/1975 | Whitehead et al. |
| D240,562 S | 7/1976 | Whitehead et al. |
| D247,370 S | 2/1978 | Whitehead |
| 4,079,739 A | 3/1978 | Whitehead |
| 4,151,240 A | 4/1979 | Lucas et al. |
| 4,272,473 A | 6/1981 | Riemersma et al. |
| 4,315,507 A | 2/1982 | Whitehead et al. |
| 4,342,314 A | 8/1982 | Radel et al. |
| 4,359,938 A | 11/1982 | Koren |
| 4,447,240 A | 5/1984 | Ito et al. |
| D276,072 S | 10/1984 | Whitehead |
| D276,073 S | 10/1984 | Whitehead |
| 4,591,523 A | 5/1986 | Thompson |
| 4,609,518 A | 9/1986 | Curro et al. |
| 4,640,859 A | 2/1987 | Hansen et al. |
| 4,798,603 A | 1/1989 | Meyer et al. |
| 4,801,494 A | 1/1989 | Datta et al. |
| 4,809,493 A | 3/1989 | Genba et al. |
| 4,834,733 A | 5/1989 | Huntoon et al. |
| 4,859,519 A | 8/1989 | Cabe, Jr. et al. |
| 4,892,534 A | 1/1990 | Datta et al. |
| 4,908,026 A | 3/1990 | Sukiennik et al. |
| 4,978,486 A | 12/1990 | Ito et al. |
| 5,074,856 A | 12/1991 | Coe et al. |
| 5,181,563 A | 1/1993 | Amaral |
| 5,248,309 A | 9/1993 | Serbiak et al. |
| 5,370,764 A | 12/1994 | Alikhan |
| 5,397,316 A | 3/1995 | LaVon et al. |
| 5,415,640 A | 5/1995 | Kirby et al. |
| 5,429,630 A | 7/1995 | Beal et al. |
| 5,614,295 A | 3/1997 | Quincy, III et al. |
| 5,628,097 A | 5/1997 | Benson et al. |
| D392,736 S | 3/1998 | Erickson |
| 5,727,458 A | 3/1998 | Schulz |
| 5,912,194 A | 6/1999 | Everhart et al. |
| 5,997,986 A | 12/1999 | Turi et al. |
| D425,985 S | 5/2000 | Velazquez et al. |
| D426,303 S | 6/2000 | Weyenberg |
| 6,093,871 A | 7/2000 | Takai et al. |
| D430,292 S | 8/2000 | Orschel et al. |
| D430,665 S | 9/2000 | Daniels et al. |
| D438,958 S | 3/2001 | Velazquez et al. |
| D439,661 S | 3/2001 | Velazquez et al. |
| 6,228,462 B1 | 5/2001 | Lee et al. |
| 6,231,555 B1 | 5/2001 | Lynard et al. |
| 6,262,331 B1 | 7/2001 | Nakahata et al. |
| D448,476 S | 9/2001 | Page et al. |
| 6,293,935 B1 | 9/2001 | Kimura et al. |
| 6,319,239 B1 | 11/2001 | Daniels et al. |
| 6,350,711 B1 | 2/2002 | Potts et al. |
| 6,436,081 B1 | 8/2002 | Wada et al. |
| 6,452,063 B1* | 9/2002 | Curro et al. ............... 604/383 |
| 6,547,774 B2 | 4/2003 | Ono et al. |
| 6,551,297 B2 | 4/2003 | Tanaka et al. |
| D478,661 S | 8/2003 | Levy et al. |
| 6,616,646 B2 | 9/2003 | Wada et al. |
| D482,786 S | 11/2003 | Harriz |
| 6,664,436 B2 | 12/2003 | Topolkaraev et al. |
| D484,973 S | 1/2004 | Costea et al. |
| 6,689,935 B2 | 2/2004 | Chen et al. |
| 7,056,404 B2 | 6/2006 | McFall et al. |
| 7,067,711 B2 | 6/2006 | Kuroda et al. |
| D533,271 S | 12/2006 | Haersjoe |
| D546,443 S | 7/2007 | Persson |
| D546,444 S | 7/2007 | Persson |
| 7,323,072 B2 | 1/2008 | Engelhart et al. |
| 7,388,123 B2 | 6/2008 | Cowell et al. |
| 7,390,553 B2 | 6/2008 | Muth et al. |
| D581,523 S | 11/2008 | Macaulay et al. |
| D581,524 S | 11/2008 | Macaulay et al. |
| D583,466 S | 12/2008 | Dobrin et al. |
| D583,934 S | 12/2008 | Li et al. |
| D584,402 S | 1/2009 | Francoeur et al. |
| D584,403 S | 1/2009 | Francoeur et al. |
| 7,491,864 B2 | 2/2009 | Nishizawa et al. |
| 7,530,973 B2 | 5/2009 | Tanio et al. |
| D594,973 S | 6/2009 | Francoeur |
| D600,805 S | 9/2009 | Hood et al. |
| D601,245 S | 9/2009 | Cauwood et al. |
| 7,597,690 B2 | 10/2009 | Tanio et al. |
| 7,621,899 B2 | 11/2009 | Fujikawa et al. |
| 7,628,777 B2 | 12/2009 | Kondo et al. |
| D607,998 S | 1/2010 | Persson |
| 7,686,790 B2 | 3/2010 | Rasmussen et al. |
| D613,856 S | 4/2010 | Mason, Jr. |
| 7,781,640 B2 | 8/2010 | Davis et al. |
| 7,847,145 B2 | 12/2010 | Kurita et al. |
| 8,030,535 B2 | 10/2011 | Hammons et al. |
| D651,306 S | 12/2011 | Misiti et al. |
| 8,071,837 B2 | 12/2011 | Saeki et al. |
| D651,708 S | 1/2012 | Misiti et al. |
| 2003/0171730 A1 | 9/2003 | Kelly et al. |
| 2003/0187418 A1 | 10/2003 | Kudo et al. |
| 2004/0163783 A1 | 8/2004 | Muller |
| 2005/0074584 A1 | 4/2005 | Zehner et al. |
| 2005/0124953 A1 | 6/2005 | Woltman et al. |
| 2005/0131369 A1 | 6/2005 | Benson |
| 2006/0087053 A1 | 4/2006 | O'Donnell et al. |
| 2007/0029694 A1 | 2/2007 | Cree et al. |
| 2007/0087169 A1 | 4/2007 | McFall |
| 2008/0004581 A1 | 1/2008 | Babusik et al. |
| 2008/0172020 A1 | 7/2008 | Schmitz |
| 2008/0249495 A1 | 10/2008 | Di Virgilio et al. |
| 2008/0294135 A1 | 11/2008 | Hara et al. |
| 2009/0026651 A1 | 1/2009 | Lee et al. |
| 2009/0054860 A1 | 2/2009 | Young et al. |
| 2009/0062764 A1 | 3/2009 | MacDonald et al. |
| 2009/0306614 A1 | 12/2009 | Boissier |
| 2009/0306615 A1 | 12/2009 | Olsson |
| 2010/0152692 A1 | 6/2010 | Ong et al. |
| 2010/0178456 A1 | 7/2010 | Kuroda et al. |
| 2010/0230866 A1 | 9/2010 | Gray et al. |
| 2010/0280471 A1 | 11/2010 | Shah |
| 2011/0223278 A1 | 9/2011 | Van Valkenburgh et al. |
| 2012/0143163 A1 | 6/2012 | Ng |
| 2012/0157949 A1* | 6/2012 | Knight et al. ............... 604/361 |
| 2012/0296303 A1 | 11/2012 | Ng et al. |

FOREIGN PATENT DOCUMENTS

| | | |
|---|---|---|
| GB | 2 089 214 A | 6/1982 |
| JP | H06-121810 | 5/1994 |
| JP | H11-178852 | 7/1999 |
| JP | 2001-314446 | 11/2001 |
| JP | 2006-051211 | 2/2006 |
| JP | 2006-334113 | 12/2006 |
| JP | 2007-089818 | 4/2007 |
| JP | 2008-023248 | 2/2008 |
| WO | WO 97/40798 | 11/1997 |
| WO | WO 98/00082 | 1/1998 |
| WO | WO 98/51250 | 11/1998 |
| WO | WO 00/35400 | 6/2000 |
| WO | WO 01/71081 | 9/2001 |
| WO | WO 2007116346 A1 | 10/2007 |
| WO | WO 2010/070503 A2 | 6/2010 |
| WO | WO 2010/070503 A3 | 6/2010 |
| WO | WO 2012044656 A1 | 4/2012 |

OTHER PUBLICATIONS

Chinese Design Patent—CN3192181, Sep. 22, 2000, 1 page.
Abstract of Chinese Patent—CN2471314, Jan. 16, 2002, 1 page.
Abstract of Chinese Patent—CN1694665, Nov. 9, 2005, 2 pages.
Abstract of Chinese Patent—CN1917838, Feb. 21, 2007, 1 page.
Abstract of Chinese Patent—CN101090689, Dec. 19, 2007, 2 pages.
Abstract of Chinese Patent—CN101674795, Mar. 17, 2010, 1 page.
Spanish Design Patent—ESD0025203, Mar. 10, 1998, 1 page.
EU Design Patent—EU000212212-0001, Aug. 2, 2004, 1 page.
EU Design Patent—EU000824313-0001, Nov. 12, 2007, 2 pages.
EU Design Patent—EU000824313-0005, Nov. 12, 2007, 2 pages.
EU Design Patent—EU000824313-0007, Nov. 12, 2007, 2 pages.
EU Design Patent—EU000824313-0011, Nov. 12, 2007, 2 pages.
EU Design Patent—EU000824313-0012, Nov. 12, 2007, 2 pages.

(56) References Cited

OTHER PUBLICATIONS

EU Design Patent—EU000824313-0014, Nov. 12, 2007, 2 pages.
EU Design Patent—EU000824313-0018, Nov. 12, 2007, 2 pages.
Abstract of Japanese Patent—JP2004041339, Dec. 2, 2004, 2 pages.
Abstract of WO Patent—WO 03/065952 A1, Aug. 14, 2003, 2 pages.
Search Report and Written Opinion for PCT/IB2012/051839 dated Nov. 23, 2012, 11 pages.
Abstract of Chinese Patent—CN2527254, Dec. 25, 2002, 1 page.
Abstract of Chinese Patent—CN301411655S, Dec. 15, 2010, 2 page.
Abstract of WO Patent—WO03103556, Dec. 18, 2003, 2 pages.
Abstract of WO Patent—WP2011118473, Sep. 29, 2011, 1 page.
Abstract of Taiwanese Patent—TWD125220S, Oct. 1, 2008, 1 page.

* cited by examiner

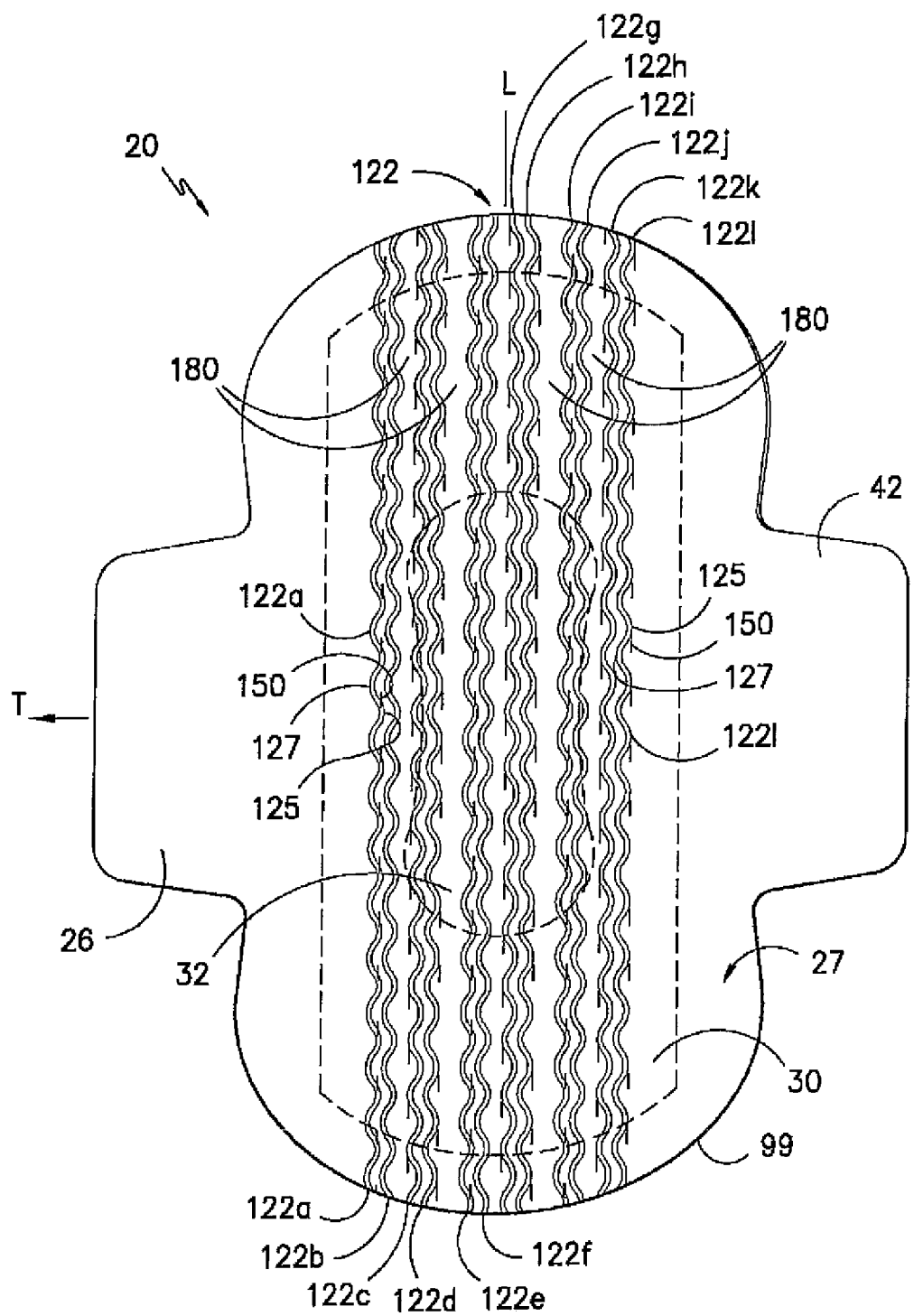
FIG. —1—

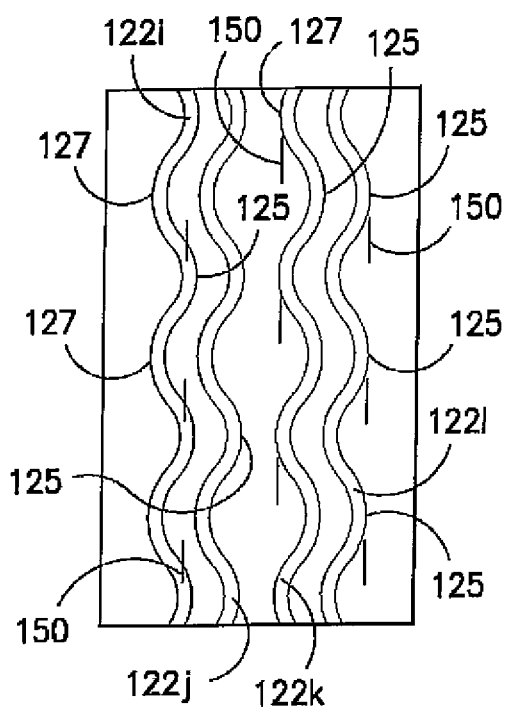
FIG. -2-
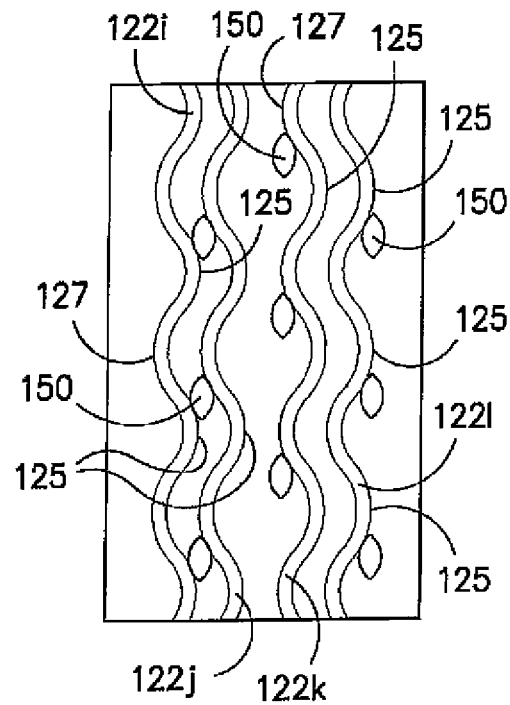
FIG. -3-
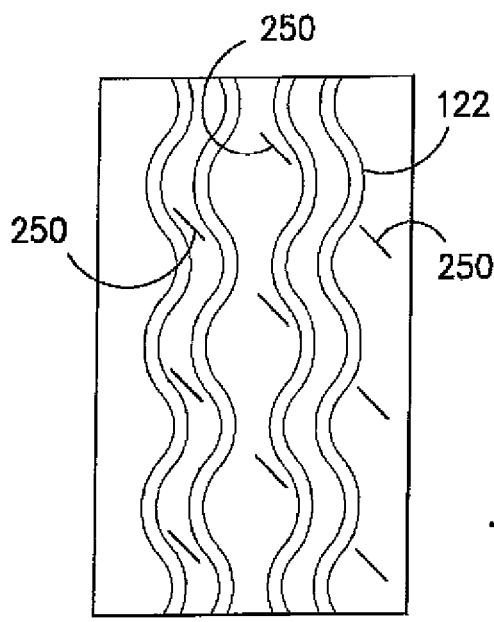
FIG. -4-

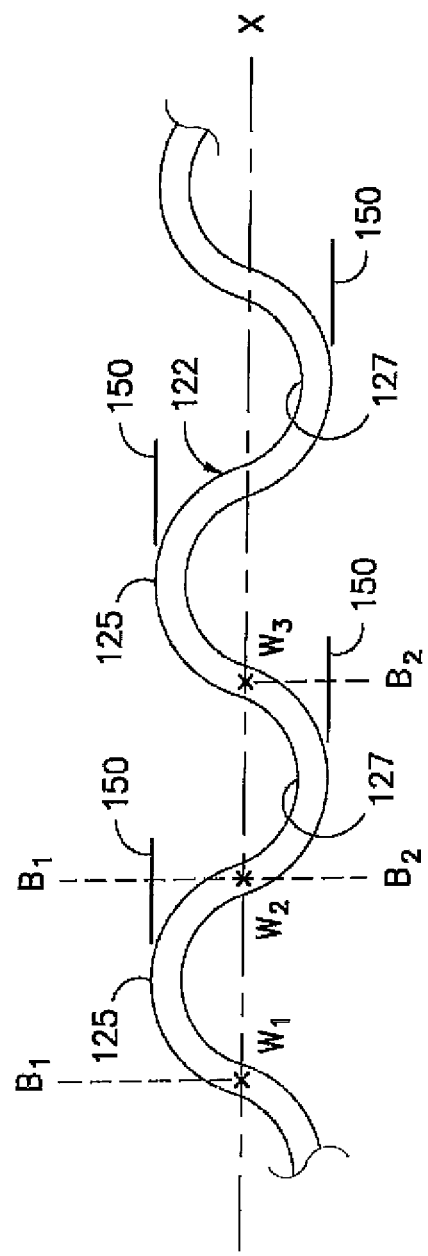
FIG. -5-

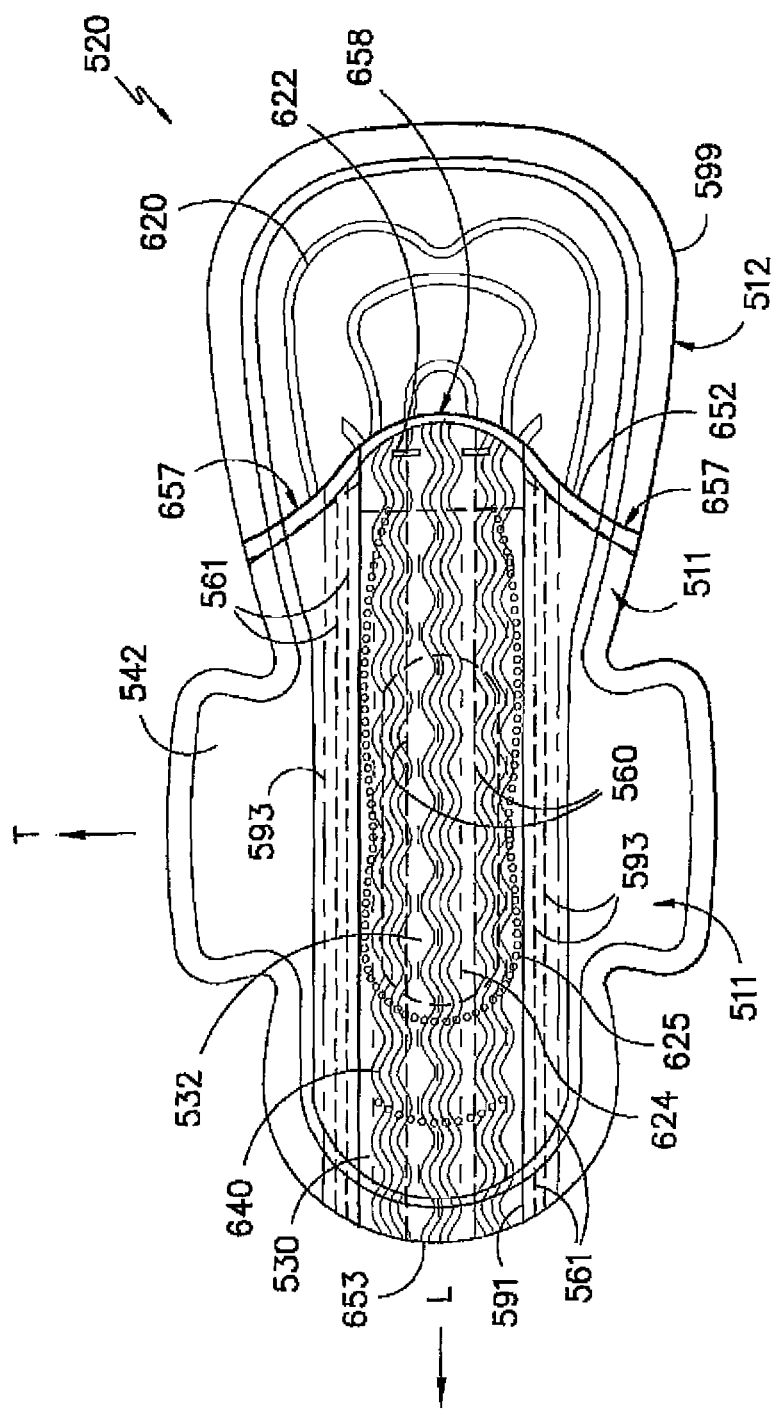
FIG. -6-

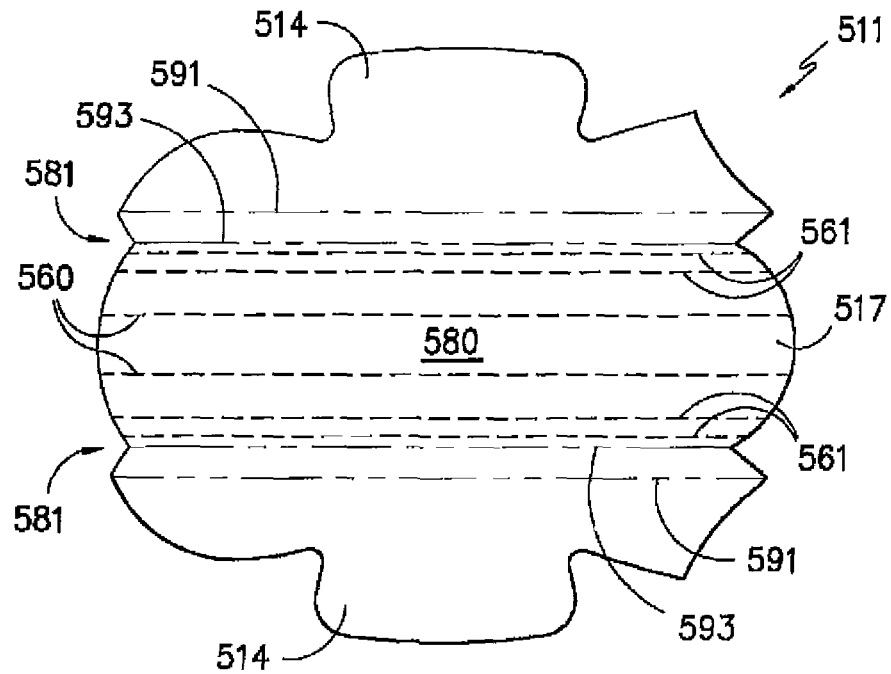
FIG. -7-
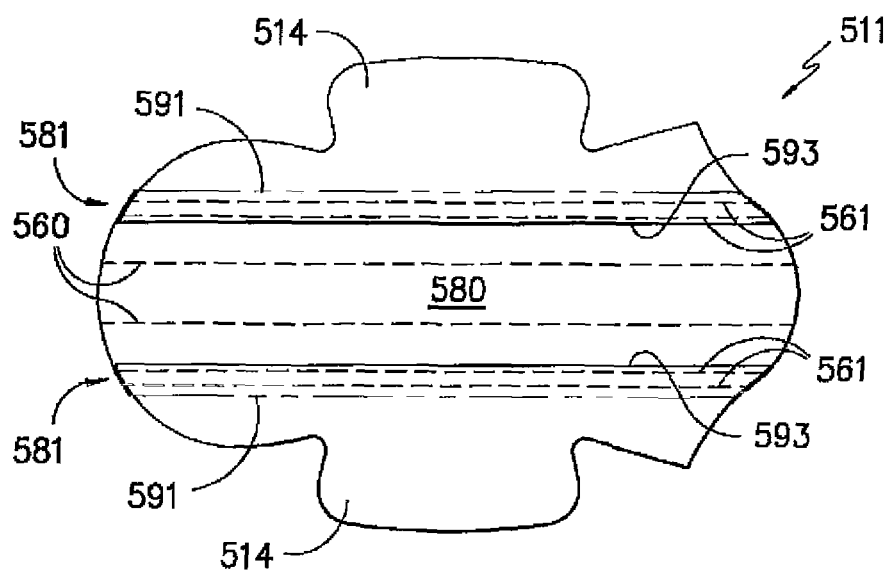
FIG. -8-

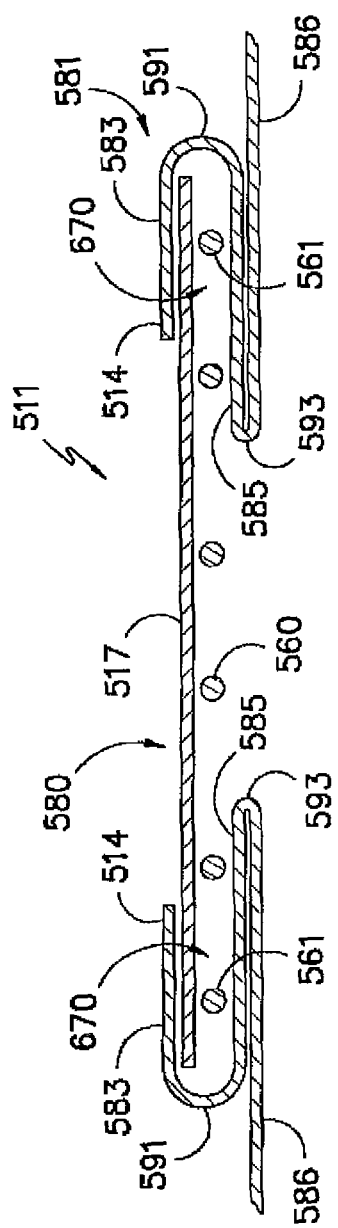
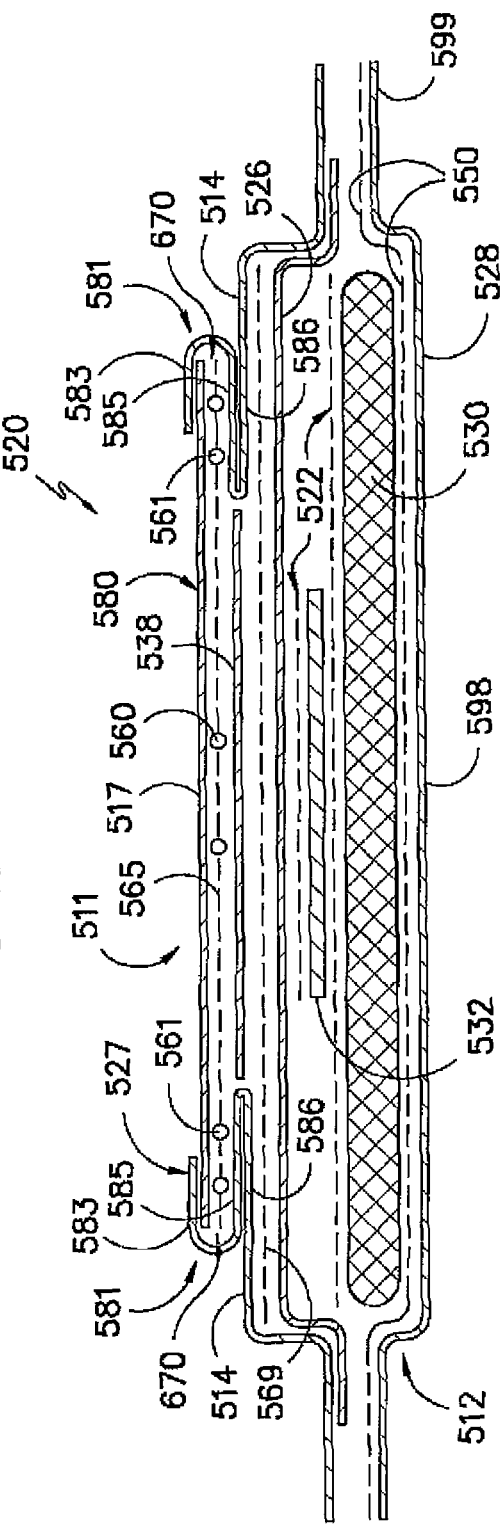

ABSORBENT ARTICLE CONTAINING APERTURES ARRANGED IN REGISTRATION WITH AN EMBOSSED WAVE PATTERN

BACKGROUND OF THE INVENTION

Absorbent articles, such as sanitary napkins, pantiliners, and incontinent pads are devices that are typically worn in the crotch region of an undergarment. Sanitary napkins and pantiliners are, for example, worn by women in a pair of panties that is normally positioned between the wearer's legs, adjacent to the perineum area. Sanitary napkins and pantiliners are designed to absorb and retain body fluids or discharges (e.g., menses) from the body of women and to prevent body and clothing from soiling. These products have developed to the extent that body exudates are quickly drawn and retained away from the wearer's skin so that the wearer remains relatively dry and comfortable. Although this improved performance enhances wearer dryness and comfort, the article can still be subject to leakage around the edges of the absorbent article, which can lead to soiling of the wearer's undergarment or clothing. This is particularly problematic in that fluid insult gushes can occur at virtually any time when the product is worn and at virtually any location (e.g., front, back, or sides of the product).

To help prevent such leakage, it is generally desirable to absorb the fluids in a central region of the article. In traditional articles, however, this is not possible as there is no barrier to bulk flow or capillary wicking from the target region (the place where intake of fluids occurs) to the edges of the pad. Thus, fluid entering the center of the pad still has the potential to travel to the edges and cause leakage. Flow from the center to the sides can be especially rapid when the article is already partially filled with fluid. In an attempt to address the problem of leakage, three-dimensional structures have been employed to enhance body fit and capture excess fluid. While these structures may add a certain level of barrier protection to the initial product, they can be easily flattened by compressional forces imparted during use. Notably, the flattening of the three-dimensional structures often occurs before the onset of a fluid insult, thereby eliminating the entire purpose of leakage control feature. Another problem with such structures is that they do not provide a consistent level of fit and fluid handling from the moment that a woman puts the article on until she removes it many hours later when it is saturated with fluid.

As such, a need exists for an absorbent article that is capable of providing better leak protection, particularly after a fluid insult.

SUMMARY OF THE INVENTION

In accordance with one embodiment of the present invention, an absorbent article is disclosed that extends in a longitudinal direction and transverse direction and defines a longitudinal centerline and a transverse centerline. The article comprises a topsheet, baffle, and an absorbent core disposed between the topsheet and the baffle. The topsheet contains an embossed region that propagates substantially in the longitudinal direction of the article in the form of a wave having alternating crests and troughs. A plurality of apertures are formed in the topsheet that are arranged in a column extending substantially in the longitudinal direction of the article. At least a portion of the apertures are located proximate to contiguous crests and/or contiguous troughs of the embossed region.

In accordance with another embodiment of the present invention, a method for forming a topsheet of an absorbent article is disclosed that extends in a longitudinal direction. The method comprises embossing the topsheet to form an embossed region that propagates substantially in the longitudinal direction in the form of a wave having alternating crests and troughs; and forming a plurality of apertures in the topsheet in a column extending substantially in the longitudinal direction. At least a portion of the apertures are located proximate to contiguous crests and/or contiguous troughs of the embossed region.

In accordance with another embodiment of the present invention, an absorbent article that extends in a longitudinal direction and transverse direction and defines a longitudinal centerline and a transverse centerline is disclosed. The article comprises a topsheet, baffle, and an absorbent core disposed between the topsheet and the baffle. The topsheet contains multiple embossed regions that propagate substantially in the longitudinal direction of the article in the form of a wave having alternating crests and troughs. Multiple slits are formed in the topsheet that are arranged in multiple columns that extend substantially in the longitudinal direction of the article. At least a portion of the slits are located proximate to contiguous crests and/or contiguous troughs of the embossed regions.

Other features and aspects of the present invention are discussed in greater detail below.

BRIEF DESCRIPTION OF THE FIGURES

A full and enabling disclosure of the present invention, including the best mode thereof, directed to one of ordinary skill in the art, is set forth more particularly in the remainder of the specification, which makes reference to the appended figures in which:

FIG. 1 is a top view of one embodiment of the absorbent article of the present invention that contains a topsheet provided with embossed wave regions in registration with apertures;

FIG. 2 is an exploded view of the embossed wave regions and apertures shown in FIG. 1;

FIG. 3 is an exploded view of the embossed wave regions and apertures of FIG. 2 after the apertures have expanded during use;

FIG. 4 is an exploded view of another embodiment of the absorbent article of the present invention in which the apertures are arranged at an angle relative to the embossed wave regions;

FIG. 5 is a schematic illustration of an embossed region that illustrates the proximate location of apertures relative to a crest and trough of the wave pattern;

FIG. 6 is a top view of one embodiment of the absorbent article the present invention;

FIG. 7 is a top view of one embodiment of a multi-section topsheet that may be employed in the present invention, shown in an initial unfolded configuration;

FIG. 8 shows the topsheet of FIG. 7 after being folded;

FIG. 9 is a cross-sectional view of the folded multi-section topsheet of FIG. 8; and FIG. 10 is a cross-sectional view of the absorbent article of FIG. 6.

Repeat use of reference characters in the present specification and drawings is intended to represent the same or analogous features or elements of the invention.

DETAILED DESCRIPTION OF REPRESENTATIVE EMBODIMENTS

Definitions

As used herein, the term "body-facing surface" generally refers to an outwardly facing surface of an absorbent article that is intended to be disposed toward or placed adjacent to the body of a wearer during ordinary use. This surface may be defined by a topsheet, which also includes an opposing inwardly facing surface.

As used herein, the term "garment-facing surface" generally refers to an outwardly facing surface of an absorbent article that is intended to be disposed away from the body of a wearer during ordinary use. The surface is typically placed adjacent to the wearer's undergarments when the article is worn. This surface may be defined by a baffle, which also includes an opposing inwardly facing surface.

DETAILED DESCRIPTION

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

Generally speaking, the present invention is directed to an absorbent article that contains a topsheet provided with embossed regions. The absorbent article may particularly be a feminine care article, such as a sanitary napkin, pad, tampon, etc. The embossed regions propagate in a longitudinal direction of the article in the form of a wave having one or more alternating crests (peaks) and troughs (valleys). Such a wave pattern helps slow down the flow of bodily fluid by directing it along a tortuous path defined by the densified edges rather than in a straight line. Among other things, this reduction in flow rate can help provide sufficient time for the absorbent core to absorb the fluid, which is particularly helpful when it is already partially filled with fluid. The three-dimensional topography formed by the embossed regions may also help improve the consistency of the fit and fluid handling properties of the article, both before and after a fluid insult.

Nevertheless, bodily fluids can still sometimes pool near the crests and/or troughs and result in leakage. To help counteract this tendency, the present inventors have also discovered that a plurality of apertures can be employed in the topsheet that are arranged in a column that generally extends in a longitudinal direction of the article. At least a portion of the apertures are located proximate to contiguous crests and/or contiguous troughs of the embossed region. Without intending to be limited by theory, it is believed that the registration of the apertures with contiguous crests and/or contiguous troughs of the embossed region puts them in a better position to receive bodily fluids that tend to pool around the embossed regions and thus reduce the likelihood of leakage.

Referring to FIG. 1, one particular embodiment of a feminine care absorbent article 20 of the present invention will now be described in more detail. As shown, the feminine care absorbent article 20 includes a topsheet 26, a baffle (not shown), and an absorbent core 30 positioned between the topsheet 26 and the baffle. The topsheet 26 defines a body-facing surface 27 of the absorbent article 20. The absorbent core 30 is positioned inwardly from the outer periphery of the absorbent article 20 and includes a body-facing side positioned adjacent the topsheet 26 and a garment-facing surface positioned adjacent the baffle. Typically, the topsheet and the baffle are joined by adhesive bonding, ultrasonic bonding, or any other suitable joining method known in the art, the sealed edges defining an overall sealed peripheral edge 99 of the article 20. The article 20 may take on various geometries but will generally have opposite lateral sides and longitudinal ends.

The topsheet 26 helps provide comfort and conformability, and also helps to direct bodily exudates away from the body toward the absorbent core 30. The topsheet 26 is liquid-permeable and has an outwardly facing surface that may contact the body of the wearer and receive aqueous fluids from the body. The topsheet may be formed from one or multiple layers of materials. The topsheet 26 retains little or no liquid in its structure so that it provides a relatively comfortable and non-irritating surface next to the tissues within the vestibule of a female wearer.

The topsheet 26 can be constructed of any woven or non-woven material that is easily penetrated by bodily exudates contacting the surface of the baffle. Examples of suitable materials include rayon, bonded carded webs of polyester, polypropylene, polyethylene, nylon, or other heat-bondable fibers, polyolefins, such as copolymers of polypropylene and polyethylene, linear low-density polyethylene, and aliphatic esters such as polylactic acid. Finely perforated film webs and net material can also be used. A specific example of a suitable topsheet material is a bonded carded web made of polypropylene and polyethylene such as that used as topsheet stock for KOTEX® pantiliners and obtainable from Sandler A G (Germany). U.S. Pat. No. 4,801,494 to Datta, et al. and U.S. Pat. No. 4,908,026 to Sukiennik, et al. teach various other topsheet materials that may be used in the present invention. The topsheet typically has a basis weight of less than about 100 grams per square meter (gsm), and in some embodiments, from about 10 gsm to about 40 gsm.

The baffle (not shown) is generally liquid-impermeable and designed to face the inner surface, i.e., the crotch portion of an undergarment. The baffle may permit a passage of air or vapor out of the absorbent article 20, while still blocking the passage of liquids. Any liquid-impermeable material may generally be utilized to form the baffle. For example, one suitable material that may be utilized is a microporous polymeric film, such as polyethylene or polypropylene. In particular embodiments, a polyethylene film is utilized that has a thickness in the range of about 0.2 mils to about 5.0 mils, and particularly between about 0.5 to about 3.0 mils. A specific example of a baffle material is a polyethylene film such as that used in KOTEX® pantiliners and obtainable from Pliant Corporation, Schaumburg, Ill., USA.

As indicated above, an absorbent core 30 is positioned between the topsheet 26 and the baffle that provides capacity to absorb and retain bodily exudates. The absorbent core 30 may be formed from a variety of different materials and contain any number of desired layers. For example, the core 30 typically includes one or more layers of an absorbent web material of cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic and hydrophilic materials, pigments, lotions, odor control agents or the like, as well as combinations thereof. In a particular embodiment, the absorbent web material includes a matrix of cellulosic fluff, and may also include superabsorbent material. The cellulosic fluff may comprise a blend of wood pulp fluff. One preferred type of fluff is identified with the trade designation NB 416, available from Weyerhaeuser Corp., and is a bleached, highly absorbent wood pulp containing primarily soft wood fibers. The absorbent materials may be formed into a web structure by employing various conventional methods and techniques. For example, the absorbent web may be formed with a dry-forming technique, an air forming technique, a wet-forming technique, a foam-forming technique, or the like, as well as combinations thereof. A coform nonwoven material may also be employed. Methods and apparatus for carrying out such techniques are well known in the art.

The topsheet 26 may be maintained in secured relation with the absorbent core 30 by bonding all or a portion of the adjacent surfaces to one another. A variety of bonding mechanisms known to one of skill in the art may be utilized to achieve any such secured relation. Examples of such mechanisms include, but are not limited to, the application of adhesives in a variety of patterns between the two adjoining surfaces, entangling at least portions of the adjacent surface of the absorbent with portions of the adjacent surface of the cover, or fusing at least portions of the adjacent surface of the cover to portions of the adjacent surface of the absorbent. The topsheet 26 typically extends over the upper, bodyside surface of the absorbent core 30, but can alternatively extend around the article to partially or entirely, surround or enclose the absorbent core. Alternatively, the topsheet 26 and the baffle can have peripheral margins that extend outwardly beyond the terminal, peripheral edges of the absorbent core 30, and the extending margins can be joined together to partially or entirely, surround or enclose the absorbent core.

Although not required, the absorbent article 20 may also contain other additional layers as is known in the art. In FIG. 1, for example, a liquid-permeable intake layer 32 is positioned vertically between the topsheet 26 and the absorbent core 30. The intake layer 32 may be made of a material that is capable of rapidly transferring, in the z-direction, body fluid that is delivered to the topsheet 26. The intake layer 32 may generally have any shape and/or size desired. In one embodiment, the intake layer 32 has a generally ovular shape, with a length equal to or less than the overall length of the absorbent article 20, and a width less than the width of the absorbent article 20. For example, a length of between about 150 mm to about 300 mm and a width of between about 10 mm to about 60 mm may be utilized. Any of a variety of different materials are capable of being used for the intake layer 32 to accomplish the above-mentioned functions. The material may be synthetic, cellulosic, or a combination of synthetic and cellulosic materials. For example, airlaid cellulosic tissues may be suitable for use in the intake layer 32. The airlaid cellulosic tissue may have a basis weight ranging from about 10 grams per square meter (gsm) to about 300 gsm, and in some embodiments, between about 40 gsm to about 150 gsm. The airlaid tissue may be formed from hardwood and/or softwood fibers. The airlaid tissue has a fine pore structure and provides an excellent wicking capacity, especially for menses.

The absorbent article 20 may also contain a transfer delay layer (not shown) positioned between the intake layer 32 and the absorbent core 30. The transfer delay layer may contain a material that is substantially hydrophobic, such as a nonwoven web composed of polypropylene, polyethylene, polyester, etc. One example of a material suitable for the transfer delay layer is a spunbond web composed of polypropylene, multi-lobal fibers. Further examples of suitable transfer delay layer materials include spunbond webs composed of polypropylene fibers, which may be round, tri-lobal or poly-lobal in cross-sectional shape and which may be hollow or solid in structure. Typically the webs are bonded, such as by thermal bonding, over about 3% to about 30% of the web area. Other examples of suitable materials that may be used for the transfer delay layer are described in U.S. Pat. No. 4,798,603 to Meyer, et al. and U.S. Pat. No. 5,248,309 to Serbiak, et al. To adjust performance, the transfer delay layer may also be treated with a selected amount of surfactant to increase its initial wettability. The transfer delay layer typically has a basis weight less than that of the other absorbent members. For example, the basis weight of the transfer delay layer is typically less than about 250 grams per square meter (gsm), and in some embodiments, between about 40 gsm to about 200 gsm.

The absorbent article 20 may also include laterally extending wing portions 42 that may be integrally connected to side regions along the intermediate portion of the article. For example, the wing portions 42 may be separately provided members that are subsequently attached or otherwise operatively joined to the intermediate portion of the article. In other configurations, the wing portions may be unitarily formed with one or more components of the article. As representatively shown in FIG. 1, for example, either or both wing portions 42 may be formed from a corresponding, operative extension of the material employed to form the topsheet 26. Alternatively, either or both wing portions 42 may be formed from a corresponding, operative extension of the material employed to form the baffle, or formed from a corresponding, operative combination of the topsheet and baffle materials.

Regardless of the particular configuration of the layers used in forming the absorbent article 20, an embossed pattern and a plurality of apertures are provided in registration. Referring to FIGS. 1-2, for example, one particular embodiment of the topsheet 26 is shown that contains embossed regions 122 and apertures 150 on the body-facing surface 27. The embossed regions 122 are generally densified regions that are positioned between un-embossed areas 180, which are not densified. This creates a three-dimensional surface topography that can increase available surface area and further improve the ability of the topsheet to take in bodily fluids and inhibit leakage. The surface topography can also improve the consistency of the fit and fluid handling properties of the article, both before and after a fluid insult.

Any number of embossed regions may be employed in the present invention, such as 1 or more, in some embodiments 2 or more, in some embodiments from 3 to 20, and in some embodiments, from 5 to 15. In FIG. 1, for example, the topsheet 26 contains twelve (12) individually spaced apart embossed regions 122 labeled as elements 122*a*, 122*b*, 122*c*, 122*d*, 122*e*, 122*f*, 122*g*, 122*h*, 122*i*, 122*j*, 122*k*, and 122*l*. Each of the embossed regions 122 shown in FIG. 1 is provided with the same pattern, but this is by no means a requirement of the present invention. In certain embodiments, for example, one or more of the regions may have a wave pattern with a different frequency, amplitude, and/or wavelength. Likewise, one or more of the embossed regions may also be arranged in a pattern that is not wavelike in nature, such as a longitudinal channel. It is typically desired that the embossed regions 122 are arranged in a generally symmetrical manner about a longitudinal centerline "L" and/or transverse centerline "T" of the topsheet 26. In the embodiment shown, for example, embossed regions 122*f* and 122*g* are disposed symmetrically about the longitudinal centerline "L", embossed regions 122*e* and 122*h* are disposed outwardly from the embossed regions 122*f* and 122*g*, embossed regions 122*d* and 122*i* are disposed outwardly from the embossed regions 122*e* and 122*h*, embossed regions 122*c* and 122*j* are disposed outwardly from the embossed regions 122*d* and 122*i*, embossed regions 122*b* and 122*k* are disposed outwardly from the embossed regions 122*c* and 122*j*, and embossed regions 122*a* and 122*l* are disposed outwardly from the embossed regions 122*b* and 122*k* and define the exterior perimeter of the embossed pattern. Although not required, the embossed regions 122 may be arranged in sets (e.g., pairs) to further enhance aesthetic appeal.

Regardless of their particular arrangement, the embossed regions 122 are defined by densified edges that extend in a wave pattern of alternating crests 125 and troughs 127 along the longitudinal direction of the topsheet 26. For sake of convenience, the term "crests" refers to peaks facing toward the right side of the topsheet shown in FIG. 1, and the "troughs" refers to peaks facing the left side. Although a sinusoidal wave pattern is depicted, it should be understood that other known wave patterns may be employed, such as sawtooth waves, square waves, triangle waves, etc. The pattern of the embossed regions 122 may be a regular periodic wave in that the wavelength (e.g., distance between contiguous crests and/or contiguous troughs) and amplitude (e.g., difference in height between a crest and trough) remain substantially constant as shown in FIG. 1. In certain embodiments, however, the pattern may also be an irregular wave in that the wavelength and/or amplitude may vary at different points of the wave. The wave pattern of the embossed regions 122 may also be continuous (e.g., without interruption), as shown in FIGS. 1-2, or discontinuous in nature. A discontinuous pattern may be for example made of dots, broken lines or other interrupted elements. The number of elements per unit length does not need to be constant but may vary along the length of the pattern or across the different discontinuous patterns when more than one are present. Although not necessarily required, it is often desired that the pattern, whether continuous or discontinuous, extends along substantially the entire length of the topsheet 26.

The topsheet 26 also contains apertures 150 that are arranged proximate to contiguous crests 125 and/or contiguous troughs 127 of at least one of the embossed regions 122. By "proximate", it is generally meant that an aperture is located on the same side of the longitudinal axis of the wave as the crest or trough, and at least a portion of the aperture is also located within a wavelength boundary defined by the crest or trough. Referring to FIG. 5, for instance, an exemplary wave embossed region 122 is shown that contains crests 125 positioned one side of a longitudinal axis of the wave (−x axis) and troughs 127 located on the other side of the axis. For exemplary purposes, a crest 125 is shown as having a wavelength boundary $B_1$ defined between points $W_1$ and $W_2$ and a trough 127 is shown as having a wavelength boundary $B_2$ defined between points $W_2$ and $W_3$. One of the apertures 150 is considered "proximate" to the crest 125 because it is located on the same side of the −x axis as the crest 125 and also extends between its wavelength boundary, $B_1$. Likewise, another of the apertures 150 is considered "proximate" to the trough 127 because it is located on the same side of the −x axis as the trough 127 and also extends between its wavelength boundary, $B_2$. Typically, a substantial portion of a given aperture is located within the wavelength boundary of a crest and/or trough, such as about 30% or more, in some embodiments about 40% or more, in some embodiments about 50% or more, and in some embodiments from about 60% to 100% of the length of the aperture.

Generally speaking, the apertures extend in substantially the same direction as the embossed region to which they are proximately located. For example, the apertures 150 of FIGS. 1-2 are arranged in columns that generally extend in the same longitudinal direction "L" as the embossed regions 122. If desired, the apertures may be positioned in a column that is tangent to the crests and/or troughs of an embossed region. The particular spacing or location of apertures within a given column may vary as desired, so long as at least a portion of the apertures are located proximate to continuous crests and/or troughs. In FIG. 2, for instance, each of the apertures 150 in one column are located proximate to contiguous crests 125 of the embossed regions 122*i* and 122*l*, and each of the apertures 150 in another column are located proximate to contiguous troughs 127 of the embossed region 122*k*. It should also be understood that apertures need not be positioned proximate to each embossed region present on the topsheet. For example, in FIG. 2, no apertures are located proximate to the embossed region 122*j*. However, it is typically desired that of those apertures provided in the topsheet, most if not all are located proximate to contiguous crests and/or troughs so that they are all in registration with the embossed region.

The apertures may possess any desired shape or size, such as circular, elliptical, triangular, rectangular, square, slits, etc. Although not required, it is often desired that the apertures are elongated. In the embodiment shown in FIGS. 1-2, for example, the apertures 150 are in the form of elongated slits having a large aspect ratio (length divided by width), such as about 5 or more, in some embodiments about 10 or more, and in some embodiments, from about 20 to about 1000. One benefit of such elongated slits is that, when disposed in registration with the embossed regions, the resulting topsheet can provide a unique aesthetic appeal. Nevertheless, during use of the absorbent article, the handling of the article and movement of the wearer may cause the topsheet to bend and stretch, thereby resulting in the expansion of the slits into larger apertures. Referring to FIG. 3, for example, the apertures 150 are shown in their expanded form. Because they are disposed adjacent to contiguous crests 125 and/or troughs 127, the expanded apertures 150 are in a position to better receive bodily fluids that tend to pool near the embossed regions 122.

In the embodiment depicted in FIGS. 1-2, the apertures 150 possess a major axis oriented in the longitudinal direction "L" of the article and a minor axis in the transverse direction "T." In this manner, the apertures themselves extend in the same longitudinal direction "L" as the embossed regions 122 and are optionally positioned tangent to the crests and/or troughs of the embossed regions. As emphasized above, this particular geometric configuration can enhance both the aesthetic appeal and absorbent properties of the article. Nevertheless, it should be understood that the apertures need not be oriented in this particular fashion. Referring to FIG. 4, an alternative embodiment of the present invention is shown in which apertures 250 possess a major axis that is oriented at an angle relative to the embossed regions 122 and the longitudinal direction "L" of the article. The angle may, for example, range from 0° to about 180°, in some embodiments from about 10° to about 70°, and in some embodiments, from about 20° to about 60°. While the individual apertures 250 are oriented at an angle, however, they are nevertheless positioned together in a column that extends in substantially the same direction as embossed regions 122 (e.g., the longitudinal direction "L"), and optionally tangent to the crests 125 and/or troughs 127.

The embossed regions and apertures described above may be formed using any known conventional techniques known in the art. Suitable techniques include, for instance, the use of raised elements to impart the desired pattern or apertures. Male/female embossing elements may also be employed.

Thermal and/or ultrasonic bonding techniques may be employed for this purpose. For instance, a suitable process may involve thermal bonding wherein a layer is passed through two rolls (e.g., steel, rubber, etc.) in which one is engraved with an embossing and/or aperture pattern and the other is flat. One or both of the rolls may be heated. The embossed regions and apertures may be formed simultaneously or separately. In one embodiment, for example, the topsheet is initially formed with the desired apertures and then embossed.

As indicated above, the embossed regions and un-embossed regions may together form a three-dimensional surface topography on the topsheet that increases surface area and limits leakage of bodily fluids, as well as improve the consistency of the fit and fluid handling properties of the article. If desired, additional structural members may also be employed to further enhance these features. In certain embodiments, for example, the absorbent article may employ a fluid-shrinkable member, which upon fluid insult, can shrink and pull a portion of the absorbent article inwardly (i.e., toward the longitudinal and/or transverse centerline of the article). For example, the member may help pull the embossed regions of the topsheet inwardly, thereby causing them to lift into a shape that forms a closer body fit. With the closer body fit, fluid has a greater tendency to be maintained within the pad, reducing the possibility of leakage.

Any number of fluid-shrinkable members may generally be employed, such as from 1 to 20, in some embodiments from 2 to 15, and in some embodiments from 4 to 10. The fluid-shrinkable members can be in the form of yarn, fiber, filament, tape, film, nonwoven, laminate, etc. Such materials are described in more detail in U.S. Patent Application Publication No. 2010/0152692 to Ong, et al., which is incorporated herein in its entirety by reference thereto for all relevant purposes. In desirable aspects, the fluid-shrinkable members have a high ratio of length to width (e.g., diameter) so that they are in the form of a string. For example, the aspect ratio may be about 10 or more, in some embodiments about 40 or more, and in some embodiments, about 100 or more.

Regardless of their form, the fluid-shrinkable members may demonstrate shrinkage ability in water, urine, menstrual fluid, etc. Shrinkage of at least about 10%, such as at least about 20%, or at least about 40%, or from about 40% to about 60% or more by length is suitable. Suitable materials for the fluid-shrinkable member include polyolefins (e.g., polyethylene, polypropylene, etc.), modified polyvinyl alcohol (PVA), modified cellulose fibers (e.g., cotton and rayon), such as carboxymethylated cotton, methylated cotton, ethylated cotton, hydroxyethylated cotton, sulfated cotton, sulfonated cotton, phosphated cotton, cationic cotton, amphoteric cotton, sodium acrylate-, acrylic acid-, acrylonitrile- or acrylamide-grafted cellulose fiber and crosslinked fiber thereof; wool or silk modified in the same manner as described above; modified synthetic fiber, such as a partially saponified acrylonitrile series of fiber and vinilon fiber which is partially esterified by maleic acid, carboxymethylcellulose and hydrolyzed acrylic fiber. In one particular aspect, a suitable modified PVA fluid-shrinkable member can be obtained from Kuraray Group, Japan.

If desired, the fluid-shrinkable members can include an optional amount of superabsorbent materials. Examples of suitable superabsorbent materials include poly(acrylic acid) and poly(methacrylic acid), poly(acrylamides), poly(vinyl ethers), maleic anhydride copolymers with vinyl ethers and $\alpha$-olefins, poly(vinyl pyrrolidone), poly(vinylmorpholinone), poly(vinyl alcohol), and salts and copolymers thereof. Other superabsorbent materials include unmodified natural polymers and modified natural polymers, such as hydrolyzed acrylonitrile-grafted starch, acrylic acid grafted starch, methyl cellulose, chitosan, carboxymethyl cellulose, hydroxypropyl cellulose, and the natural gums, such as alginates, xanthan gum, locust bean gum, and so forth. Mixtures of natural and wholly or partially synthetic superabsorbent polymers may also be useful in the present invention. The superabsorbent material can be present in the fluid-shrinkable member in an amount as desired, provided that it does not diminish the effectiveness of the shrinkable member. For example, in some aspects, the fluid-shrinkable members can contain up to about 1 wt. %, such as up to about 5 wt. %, or even up to about 10 wt. % or more superabsorbent material to provide improved benefits.

The fluid-shrinkable members can also include an optional elastomeric polymer having a permeability for water vapor to facilitate moisture absorption. The elastomeric polymer component may be present in an amount effective to achieve the desired dimensional change properties. The elastomeric polymer can be present in an amount as desired, provided that it does not diminish the effectiveness of the shrinkable member. For example, in some aspects, the fluid-shrinkable members can contain up to about 1 wt. %, such as up to about 5 wt. %, or even up to about 10 wt. % or more elastomeric polymer to provide improved benefits. Examples of suitable elastomeric polymers include, but are not limited to, thermoplastic polyurethanes, poly(ether-amide) block copolymers, polyolefins (e.g., polyethylene, polypropylene, etc.), styrene-butadiene copolymers, silicon rubbers, synthetic rubbers such as nitrile rubber, styrene isoprene copolymers, styrene ethylene butylene copolymers, butyl rubber, nylon copolymers, spandex fibers comprising segmented polyurethane, ethylene-vinyl acetate copolymer or mixtures thereof.

The manner in which the fluid-shrinkable member is incorporated into the absorbent article may vary as desired. In one embodiment, for example, the fluid-shrinkable member extends in a longitudinal direction of the article so that at least a portion of the member is located adjacent to an end of the topsheet. Optionally, at least a portion of the end of the topsheet remains generally unbonded to the baffle. Thus, when the fluid-shrinkable member contracts upon contacting a fluid insult, the end of the topsheet can raise outwardly from the plane of the absorbent article. The raised area creates a barrier to the leakage of fluids from the center of the article towards its end. In certain embodiments, contraction of the fluid-shrinkable member can also cause an outer region of the topsheet to rise outwardly from the plane of the absorbent article to create a barrier to the leakage of fluids from the center of the article towards the side edge. Notably, because such barriers are generally created only after contact with a fluid insult, their effectiveness is not diminished through use of the article prior to the insult.

Referring to FIGS. 6 and 10, one particular embodiment of a feminine care absorbent article 520 that employs such fluid-shrinkable members will now be described in more detail. As shown, the feminine care absorbent article 520 (e.g., feminine care pad or napkin) includes a topsheet 511 that generally overlies a base pad 512. The configuration and materials used to form the base pad 512 are not generally critical, so long as it is capable of absorbing bodily fluids. In the illustrated embodiment, for example, the base pad 512 includes a liquid-permeable cover 526, a generally liquid-impermeable baffle 528, intake layer 532, and an absorbent core 530 positioned between the cover 526 and the baffle 528. The materials and techniques for joining such layers are described in more detail above. In the embodiment shown in FIG. 10, for instance, the cover 526 is bonded to the baffle 528 with an adhesive 550, which can optionally extend along a substantial length of the pad 512. If desired, the adhesive 550 may also be extended to the center of the baffle 528 so that it bonds together the baffle 528 and the absorbent core 530. Adhesives 552 may also be employed to bond the cover 526 to the intake layer 532 and the intake layer 532 to the absorbent core 530 if desired.

The topsheet 511 generally extends over the upper, bodyside surface of the base pad 512, but can alternatively extend around the article to partially or entirely, surround or enclose the base pad. Typically, the topsheet 511 and the baffle 528 of the base pad 512 have peripheral margins 599 that extend outwardly beyond the terminal, peripheral edges of the absorbent core 530, and the extending margins are joined together to partially or entirely, surround or enclose the absorbent core. The topsheet 511 contacts the body of the user and is liquid-permeable. The topsheet 511 may be formed from one or multiple layers of materials. The liquid-permeable topsheet 511 has an outwardly facing surface 527 that may contact the body of the wearer and receive fluids from the body. The topsheet 511 is provided for comfort and conformability and functions to direct bodily exudates away from the body toward the absorbent core 530.

In accordance with the present invention, the topsheet 511 also contains embossed regions 640 and apertures 624. The embossed regions 640 propagate substantially in the longitudinal direction of the article 520 in the form of a wave having alternating crests and troughs, and the apertures 624 are likewise arranged in a column extending substantially in the longitudinal direction of the article and at least a portion of the aperture are located proximate to contiguous crests and/or contiguous troughs of the embossed regions. Other types of embossed regions may also be formed in one or more layers of the article to serve a variety of different purposes. In the embodiment shown in FIGS. 6 and 10, for example, embossed regions 622 are formed in the topsheet 11. Likewise, embossed regions 620 and 625 may be formed in the base pad 512 to help guide fluids in the desired manner and create additional bulk in the article. The embossed regions 625 are formed in the absorbent core 530 and the embossed regions 620 are formed in the cover 526.

As explained above, the combination of the embossed regions 640 and apertures 624 in the topsheet can help inhibit leakage. Other aspects of the absorbent article 520 may likewise be selectively controlled to help further reduce the likelihood of leakage. For example, in certain embodiments, at least a portion of the topsheet 511 remains generally unbonded to the baffle 528. As will be explained in more detail below, this can allow for improved leakage protection during use of the article. The topsheet 511 may also define an inner region 580 positioned between laterally spaced first and second outer regions 581, which may be formed from a single section of material, or from multiple sections. In FIGS. 6 and 10, for instance, the topsheet 511 is formed from a center section 517 that is positioned between side sections 514. Such multi-section topsheet configurations are known in the art and described in more detail, for instance, in U.S. Pat. No. 5,415, 640 to Kirby, et al., which is incorporated herein in its entirety by reference thereto for all purposes.

The fluid-shrinkable members may be incorporated into the absorbent article in a selectively controlled manner to optimize the ability to reduce leakage. For example, at least one fluid-shrinkable member may be employed that generally extends in a longitudinal direction of the article and is disposed adjacent to an end of the topsheet. The placement of a fluid-shrinkable member "adjacent" to an end does not necessarily mean that the member must be directly adjacent to or terminate at the end of the topsheet. In fact, the member may terminate before and/or after reaching the end of the topsheet, so long as its contraction helps facilitate the creation of a barrier in accordance with the present invention. For example, in certain embodiments, a fluid-shrinkable member may terminate a distance of about 10 millimeters or less, in some embodiments about 5 millimeters or less, and in some embodiments, about 2 millimeters or less away from an end of the topsheet.

Referring again to FIGS. 6 and 10, for example, one embodiment of the present invention is shown in the topsheet 511 has a distal end 653 and an opposing proximal end 652. Although the proximal and distal ends are shown herein as the front and rear ends of the article, respectively, the terms "proximal" and "distal" do not necessarily refer to the rear and front ends of the topsheet as such terms are employed only for the sake of convenience. In one embodiment, for example, the term "proximal" may refer to the front end of the topsheet. In any event, the shape of the proximal and/or distal ends of the topsheet may be configured to help improve the comfort of the article during use. In the embodiment shown in FIG. 6, for example, the proximal end 652 of the topsheet 511 may have a configuration in which peripheral portions 557 taper outwardly from a central portion 558. This forms a general parabolic shape that can better conform to the body, both before and after fluid insult. Depending on the desired fit, the angle of the taper may generally range from about 10° to about 180°, and in some embodiments, from about 40° to about 80°.

Regardless, in the illustrated embodiment, a plurality of outer, fluid-shrinkable members 561 and inner, fluid-shrinkable members 560 are employed that extend in a longitudinal direction "L" and are located adjacent to the proximal end 652. The outer members 561 are also disposed adjacent to outer regions 581 of the topsheet 511, and the inner members 560 are spaced laterally inward from the outer members 561 so that they are located adjacent to the inner region 580 of the topsheet 511. By disposing fluid-shrinkable members in this manner, the end(s) and the side(s) of the topsheet are capable of rising outwardly from the plane of the absorbent article during use to create a cup-shaped barrier to the leakage of fluids from the center of the article towards the edges. The relative distance that the side(s) and/or end(s) of the topsheet are capable of being raised may vary, but is typically at least about 1 millimeter, in some embodiments at least about 4 millimeters, and in some embodiments, from about 10 to about 70 millimeters above the original plane of the article. Likewise, the angle of orientation of the side(s) and/or end(s) upon raising may range from about 1° to about 90°.

In the embodiment illustrated, at least a portion of the proximal end 652 remains generally unbonded to the base pad 512 (e.g., baffle 528) so that it is capable of forming a raised area upon contraction of the fluid-shrinkable members as described above. Although not shown, a portion of the distal end 653 may also be generally unbonded to the base pad 512 (e.g., baffle 528) so it can form a raised barrier upon the contraction a fluid-shrinkable member located proximate thereto. It should be understood that while such ends may be generally unbonded, some portion of the end can nevertheless still be joined to the base pad. In one embodiment, for example, peripheral regions 657 of the proximal end 652 may be joined to the base pad 512, while a central region 658 remains generally unbonded. In this configuration, the central region 658 of the proximal end 652 can raise outwardly from the plane of the absorbent article during use to create an additional barrier to the leakage of fluids from the center toward the end of the article. To achieve such a bonding configuration, an area that spans a distance of from about 20 to about 200 millimeters, and in some embodiments, from about 20 to about 40 millimeters from the tapered peak of the proximal end 652 to a horizontal line may remain unbonded to the base pad 512. The other areas of the topsheet 511 may be bonded to the base pad 512 using any pattern desired, such as continuous or discontinuous (e.g., toothed, stepped, dots, etc.). Any known bonding method may be employed, such as adhesive bonding, ultrasonic bonding, mechanical bonding, heat bonding, etc.

Prior to contact with bodily fluids, the topsheet 511 remains substantially flat. However, upon a gush of fluid, the contraction of the fluid-shrinkable members 560 and/or 561 pulls the proximal end 652 upwardly and in a longitudinal direction toward the center of the absorbent article 520. This creates a barrier to the leakage of fluids from the center toward the rear of the article. Contraction of the fluid-shrinkable members 561 also causes the outer regions 581 of the topsheet 511 to rise (e.g., buckle) and create a barrier to the leakage of fluids from the center toward the sides of the article. Because these barriers are created only after contact with a fluid insult, their effectiveness is not generally diminished through use of the article prior to the insult.

To facilitate the ability of the proximal end 652 of the topsheet 511 to rise up in the manner described above, the length of the topsheet 511 may be less than that of the baffle 528. For example, the ratio of the length of the topsheet 511 to the length of the baffle 528 (in the longitudinal direction) may be from about 0.2 to about 1.0, in some embodiments from about 0.3 to about 0.9, and in some embodiments, from about 0.5 to about 0.8. Nevertheless, it should be understood that the topsheet 511 may also have a length that is the same or even greater than that of the baffle 528, such as a length ratio of from about 1.0 to about 10.0. In such embodiments, it is often desired to form the proximal end and/or distal end through a cut made in the topsheet material. In one embodiment, the topsheet may extend in the longitudinal direction to a first end that is joined to the baffle and defines a length that is substantially the same as the base pad. Nevertheless, the first end may not be the proximate and/or distal end as defined herein. More particularly, a portion of the topsheet may be formed to define a second end located adjacent to the fluid-shrinkable members. This portion is generally unbonded to the base pad and is thus capable of rising up during use due to the constriction of the fluid-shrinkable member during use. Thus, in this particular embodiment, the second end is considered the "proximal" end. Any technique may generally be employed to form the second end, such as by cutting, slitting, etc. the topsheet, or by simply attaching a separate material thereto.

A variety of different techniques may be employed to incorporate the fluid-shrinkable members into the absorbent article. In one embodiment, for example, the fluid-shrinkable members may simply be attached to a garment-facing surface of the topsheet. In FIGS. 6 and 10, for example, the fluid-shrinkable members are directly connected to the topsheet 511 with an adhesive 565. Other suitable bonding techniques may also be employed, such as stitching, thermal bonds, ultrasonic bonds, embossing, crimping, entangling, fusing, etc., and combinations thereof. It should also be understood that such members may be indirectly connected to the topsheet, such as by using one or more layers that are disposed between the members and the topsheet and attached thereto. Bonding may occur over the entire length of each member. In other embodiments, however, only a portion of a member may be bonded, such as through the use of one or more spot welds. In some aspects, it is desirable to anchor the ends of the member into the article while keeping the central length of the member free from bonds to provide improved shrinkage performance.

If desired, additional techniques may be employed to help further ensure that the fluid-shrinkable members are retained in the absorbent article during use, and also to further bolster the three-dimensional topography that is achieved by the present invention. For example, in certain embodiments, the topsheet may be folded to create a pocket within which the outer members can reside. The pocket helps secure the fluid-shrinkable members and also adds bulk to the topsheet. In FIGS. 6 and 10, for instance, the outer regions 581 of the topsheet 511 are folded to create a pocket 670 within which the fluid-shrinkable members 561 are retained.

FIGS. 7-9 illustrate in more detail the manner in which the topsheet 511 can be folded to achieve the desired pocket configuration. More specifically, FIG. 7 shows the topsheet 511 in its initial unfolded configuration. To create the desired pocket, the outer regions 581 are bent inwardly along fold lines 591 so that a first portion 583 of the topsheet 511 is disposed above a second portion 585 (FIGS. 8 and 9). In this manner, the fluid-shrinkable members 561 can be sandwiched in the pocket 670 formed between the first portion 583 and second portion 585 (FIG. 9). The outer regions 581 may also be bent outwardly along fold lines 593 to create a z-shaped folded configuration in which a third portion 586 of the topsheet 511 extends generally parallel to the base pad 512. If desired, the outer members 561 may also be disposed within the pocket formed between the second portion 585 and the third portion 586. It should be noted that the referenced portions 583, 585, and 586 may be formed by one or multiple sections of the topsheet 511 as discussed above. For example, in the illustrated embodiment, each of the portions 583, 585, and 586 are formed by the side sections 514 of the topsheet 511. In alternative embodiments, however, the center section 517 may constitute the first portion, second portion, and/or third portion, and may optionally be folded to achieve the desired pocket configuration.

In certain embodiments, the manner in which the pocket 670 is formed can help facilitate the ability of the outer regions 581 to rise upwardly. For example, in one embodiment, the first portion 583 of the side section 514 can be wrapped around the center section 617 and remain generally unbonded thereto. In this manner, contraction of the members 561 forces upward the center section 617, which in turn forces upward the first portion 583. Unlike the center section 617, however, the first portion 583 is able to rise up without restriction because it is generally unbonded. It should be understood, however, that the first portion 583 can also be bonded to the center section if so desired.

In addition to the longitudinally extending fluid-shrinkable members described above, fluid-shrinkable members may also be disposed at other locations within the absorbent article and in various different configurations. In certain embodiments, for example, fluid-shrinkable members may be employed that extend in the transverse direction to form a cross-stitching pattern with longitudinally-extending members. Various other patterns that may be formed by the fluid-shrinkable members may include, for instance, diagonal patterns, wavy patterns, circular patterns, triangular patterns, etc. In addition, while the aforementioned embodiments have exemplified fluid-shrinkable members in a generally planar configuration, it should be understood that the fluid-shrinkable members can also be present at any angle from plane of the absorbent article, such as substantially perpendicular to the plane of the article (e.g., into the absorbent core).

If desired, additional materials may also be employed in the absorbent article. Referring again to FIGS. 6 and 10, for instance, a fluid distribution layer 538 may be disposed between the topsheet 511 and the base pad 512. Among other things, the fluid distribution layer 538 may add bulk to the article, which can improve the consistency of the fit and fluid handling capacity both before and after the fluid insult, as well as aid in securing the interior fluid-shrinkable members to the topsheet 511. For example, the adhesive 565 may connect the fluid-shrinkable members 560 to the center section 517 of the topsheet 511 and to the fluid distribution layer 538. The fluid distribution layer 538 may be formed from a material that is substantially hydrophobic, such as a nonwoven web composed of polypropylene, polyethylene, polyester, etc. One example of such a material is a spunbond web composed of polypropylene, bicomponent fibers, which may be round, tri-lobal or poly-lobal in cross-sectional shape and which may be hollow or solid in structure. Typically the webs are bonded, such as by thermal bonding, over about 3% to about 30% of the web area. Such materials typically have a basis weight of less than about 100 gsm, and in some embodiments, from about 10 gsm to about 40 gsm. Other examples of suitable materials that may be used for fluid distribution layer 38 are described in U.S. Pat. No. 4,798,603 to Meyer, et al. and U.S. Pat. No. 5,248,309 to Serbiak, et al. To adjust performance, the fluid distribution layer may also be treated with a selected amount of surfactant to increase its initial wettability.

In addition to fluid-shrinkable members, fluidic guides may also be employed in the present invention to assist in leakage prevention. For instance, U.S. Pat. No. 5,614,295 to Quincy, Ill, et al., which is incorporated herein in its entirety by reference thereto, describes a fibrous web that is specifically configured to distribute liquid in the direction of the orientation of the fibers. The web is formed from a first zone of fibers treated with a surfactant and a second zone of fibers exposed to a corona field. U.S. Pat. No. 7,388,123 to Cowell, et al., which is incorporated by reference, describes another suitable fluidic guide that is in the form of bands of a barrier substance material (e.g., phase change material) deposited on the topsheet along at least a portion of the periphery of the article. Still another suitable fluid guide may include a permeable sheet (e.g., nonwoven web) adsorbed with an amphiphilic protein (e.g., milk protein) to define a gradient distribution of an amphiphilic protein coating along at least one dimension of the permeable sheet. This provides controlled wettability along at least one dimension of the permeable, liquid flow control material. Such materials are described in more detail in U.S. Pat. No. 5,912,194 to Everhart, et al., which is incorporated herein in its entirety by reference thereto for all purposes. In yet another embodiment, the fluid guide may be a nonwoven web having a high basis weight and/or high denier, such as described in U.S. Pat. No. 4,892,534 to Datta, et al., which is incorporated herein in its entirety by reference thereto for all purposes. For example, the basis weight may range from about 0.5 to 1.0 ounces per square yard, and in some embodiments, from about 0.7 to 1.0 ounces per square yard, and the denier may range from about 3 to about 15, and in some embodiments, from about 4 to about 12. Such high basis weight and high denier webs contain large passageways that extend downward through the thickness of the web and have the ability to draw a greater quantity of bodily fluid away from the visible surface, thereby actively masking visible stains. The fluid guides may be employed in the center and/or periphery of the article as desired.

A chemical treatment may also be employed to alter the color of the bodily fluid should any leakage occur. In one embodiment, for example, the treatment may be a decolorizing composition that agglutinates (agglomerates) red blood cells in blood and menses and limits the extent that the red color of menses is visible. One such composition includes a surfactant, such as described in U.S. Pat. No. 6,350,711 to Potts, et al. which is incorporated herein in its entirety by reference thereto. Particular examples of such surfactants are Pluronic® surfactants (tri-block copolymer surfactant). Another suitable composition that can help agglutinate (agglomerate) the cells includes one or more inorganic salts that contain a polyvalent anion (e.g., divalent, trivalent, etc.), such as sulfate ($SO_4^{2-}$), phosphate ($PO_4^{3-}$), carbonate ($CO_3^{2-}$), oxide ($O^{2-}$), etc., and a monovalent cation, such as sodium ($Na^+$), potassium ($K^+$), lithium ($Li^+$), ammonium ($NH_4^+$), etc. Alkali metal cations are particularly desirable. Specific examples of salts formed from such ions include, for instance, disodium sulfate ($Na_2SO_4$), dipotassium sulfate ($K_2SO_4$), disodium carbonate ($Na_2CO_3$), dipotassium carbonate ($K_2CO_3$), monosodium phosphate ($NaH_2PO_4$), disodium phosphate ($Na_2HPO_4$), monopotassium phosphate ($KH_2PO_4$), dipotassium phosphate ($K_2HPO_4$), etc. Mixtures of the aforementioned salts may be particularly effective in facilitating physical separation of red blood cells. For instance, a mixture of disodium sulfate ($Na_2SO_4$) and monopotassium phosphate ($KH_2PO_4$) may be employed.

Besides agglutinating agents, the decolorizing composition may also alter the chemical structure of hemoglobin to change its color. Examples of such compositions are described in U.S. Patent Application Publication No. 2009/0062764 to MacDonald, et al., which is also incorporated herein in its entirety by reference thereto. More particularly, the composition includes an oxidizing agent that is generally capable of oxidizing hemoglobin or other substances responsible for an unwanted color of the bodily exudates. Suitable oxidizing agents may include, for instance, peroxygen bleaches (e.g., hydrogen peroxide, percarbonates, persulphates, perborates, peroxyacids, alkyl hydroperoxides, peroxides, diacyl peroxides, ozonides, supereoxides, oxo-ozonides, and periodates); hydroperoxides (e.g., tert-butyl hydroperoxide, cumyl hydroperoxide, 2,4,4-trimethylpentyl-2-hydroperoxide, di-isopropylbenzene-monohydroperoxide, tert-amyl hydroperoxide and 2,5-dimethyl-hexane-2,5-dihydroperoxide); peroxides (e.g., lithium peroxide, sodium peroxide, potassium peroxide, ammonium peroxide, calcium peroxide, rubidium peroxide, cesium peroxide, strontium peroxide, barium peroxide, magnesium peroxide, mercury peroxide, silver peroxide, zirconium peroxide, hafnium peroxide, titanium peroxide, phosphorus peroxide, sulphur peroxide, rhenium peroxide, iron peroxide, cobalt peroxide, and nickel peroxide); perborates (e.g., sodium perborate, potassium perborate, and ammonium perborate); persulphates (e.g., sodium persulphate, potassiumdipersulphate, and potassium persulphate); and so forth. Other suitable oxidizing agents are omega-3 and -6 fatty acids, such as linoleic acid, α-linoleic acid, arachidonic acid, eicosapentaenoic acid, docosahexaenoic acid, eicosadienoinc acid, eicosatrienoic acid; etc.

The decolorizing composition may be applied to any liquid-permeable layer of the absorbent article where it can contact aqueous fluids exuded by the body (e.g., menses), such as the topsheet, fluid distribution layer, cover, absorbent core, intake layer, and so forth. In one embodiment, the decolorizing composition may cover only a portion of the surface to ensure that the layer is still capable of retaining sufficient absorbent properties. In certain embodiments, it may be desired that the decolorizing composition is positioned closer to the absorbent core to minimize potential leakage. In addition to being applied to the absorbent core, other configurations may also be employed in the present invention. For example, an additional layer (not shown) may be applied with the decolorizing composition that is in contact with the absorbent core. The additional layer may be formed from a variety of different porous materials, such as a perforated film, nonwoven web (e.g., cellulosic web, spunbond web, meltblown web, etc.), foams, etc. In one embodiment, the additional layer may be in the form of a hollow enclosure (e.g., sachet, bag, etc.) that is folded so that it partially or completely surrounds the absorbent core. The decolorizing composition may be disposed within this enclosure so that it remains sealed therein prior to use. In another embodiment, however, the additional layer may be the intake layer. Typically, the decolorizing composition is disposed on a surface facing away from the absorbent core; however, it should also be understood that the decolorizing composition may be positioned on any other surface, such as between the additional layer and the absorbent core.

If desired, the absorbent article of the present invention may also be employed in conjunction with a disposable or reusable garment that is specifically tailored to fit with the absorbent article of the present invention. One example of such an undergarment/absorbent article system is described in U.S. Pat. No. 6,547,774 to Ono, et al., which is incorporated herein in its entirety by reference thereto for all purposes.

As a result of the combination of features employed in the present invention, an absorbent article may thus be formed that exhibits a reduced likelihood of leakage during use. This may be evident throughout the entire use of article, including upon an initial insult of a fluid and subsequently when the article has already absorbed a certain amount of fluid. More particularly, the embossments and/or apertures of the present invention may help facilitate the rapid intake of fluids that can occur during an initial insult. Nevertheless, even as the article fills with fluid and a portion of the absorptive capacity is depleted, the raised topsheet area(s) created by the fluid-shrinkable members in certain embodiments can still form a barrier to the leakage of fluids from the center of the article towards its edges, thereby further minimizing the likelihood of leakage.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. An absorbent article that extends in a longitudinal direction and transverse direction and defines a longitudinal centerline and a transverse centerline, wherein the article comprises:

a topsheet containing an embossed region that propagates substantially in the longitudinal direction of the article in the form of a wave having alternating crests and troughs, and further wherein a plurality of apertures are formed in the topsheet that are arranged in a column extending substantially in the longitudinal direction of the article, wherein at least a portion of the apertures are located proximate to contiguous crests and/or contiguous troughs of the embossed region, wherein the apertures are elongated and have a major axis extending in the longitudinal direction of the article, and wherein the column of apertures is oriented substantially tangent to one or more crests and/or troughs of the wave;

a baffle; and an absorbent core disposed between the topsheet and the baffle.

2. The absorbent article of claim 1, wherein each aperture in the column is located proximate to a crest or trough of the embossed region.

3. The absorbent article of claim 1, wherein the column includes only apertures that are located proximate to a crest or trough of the embossed region.

4. The absorbent article of claim 1, wherein the embossed region is continuous and extends along the entire length of the topsheet.

5. The absorbent article of claim 1, wherein the topsheet contains multiple embossed regions that propagate substantially in the longitudinal direction of the article in the form of a wave having alternating crests and troughs, and further wherein the plurality of apertures are arranged in multiple columns that extend substantially in the longitudinal direction of the article, wherein at least a portion of the apertures in each column are located proximate to contiguous crests and/or contiguous troughs of an embossed region.

6. The absorbent article of claim 5, wherein each of the embossed regions has substantially the same wave pattern.

7. The absorbent article of claim 5, wherein each of the apertures in the columns are located adjacent to a crest or trough of an embossed region.

8. The absorbent article of claim 5, wherein the embossed regions are distributed symmetrically about the longitudinal centerline of the article.

9. The absorbent article of claim 1, wherein the wave is a regular periodic wave.

10. The absorbent article of claim 9, wherein the wave is a sinusoidal wave.

11. The absorbent article of claim 1, wherein the elongated apertures are slits.

12. The absorbent article of claim 11, wherein the slits have an aspect ratio of about 5 or more.

13. The absorbent article of claim 1, wherein the major axis of the elongated apertures is substantially tangent to one or more of the crests and/or troughs of the wave.

14. The absorbent article of claim 1, wherein the major axis of the elongated apertures is oriented at an angle relative to one or more of the crests and/or troughs of the wave, wherein the angle ranges from about 10° to about 70°.

15. The absorbent article of claim 1, wherein the absorbent article further comprises a fluid-shrinkable member.

16. The absorbent article of claim 15, wherein the fluid-shrinkable member is located adjacent to the topsheet and extends in the longitudinal direction.

* * * * *

UNITED STATES PATENT AND TRADEMARK OFFICE
CERTIFICATE OF CORRECTION

| | | |
|---|---|---|
| PATENT NO. | : 8,847,002 B2 | Page 1 of 1 |
| APPLICATION NO. | : 13/111167 | |
| DATED | : September 30, 2014 | |
| INVENTOR(S) | : Priscilla Eng Choo Goh et al. | |

It is certified that error appears in the above-identified patent and that said Letters Patent is hereby corrected as shown below:

On the title page item 75 Inventors:

"Priscilla Goh Eng Goh" should read --Priscilla Eng Choo Goh--

Signed and Sealed this
Thirtieth Day of December, 2014

Michelle K. Lee
*Deputy Director of the United States Patent and Trademark Office*